(12) United States Patent  (10) Patent No.: US 8,301,267 B2
Shuros et al.  (45) Date of Patent: Oct. 30, 2012

(54) METHOD AND APPARATUS FOR SENSING MECHANICAL ENERGY OF AN IMPLANTABLE LEAD

(75) Inventors: Allan C. Shuros, St. Paul, MN (US); Dan Li, Shoreview, MN (US); Krzysztof Z. Siejko, Maple Grove, MN (US); John H. Tangren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 186 days.

(21) Appl. No.: 12/876,426

(22) Filed: Sep. 7, 2010

(65) Prior Publication Data

US 2011/0071411 A1  Mar. 24, 2011

Related U.S. Application Data

(60) Provisional application No. 61/243,683, filed on Sep. 18, 2009.

(51) Int. Cl.
*A61N 1/05* (2006.01)
(52) U.S. Cl. ........................................ 607/119; 607/115
(58) Field of Classification Search .................. 607/115, 607/116, 119
See application file for complete search history.

(56) References Cited

U.S. PATENT DOCUMENTS

| | | | |
|---|---|---|---|
| 5,496,361 A | 3/1996 | Moberg et al. |
| 5,549,650 A | 8/1996 | Bornzin et al. |
| 5,628,777 A | 5/1997 | Moberg et al. |
| 5,899,927 A | 5/1999 | Ecker et al. |
| 6,044,299 A | 3/2000 | Nilsson |
| 6,493,579 B1 | 12/2002 | Gilkerson et al. |
| 6,520,916 B1 | 2/2003 | Brennen |
| 6,980,866 B2 | 12/2005 | Yu et al. |
| 7,127,289 B2 | 10/2006 | Yu et al. |
| 2004/0133243 A1 | 7/2004 | Santamore et al. |
| 2005/0027323 A1 | 2/2005 | Mulligan et al. |
| 2005/0209649 A1 | 9/2005 | Ferek-petric |
| 2006/0161211 A1 | 7/2006 | Thompson et al. |
| 2006/0178586 A1 | 8/2006 | Dobak, III |
| 2007/0129781 A1 | 6/2007 | Yu et al. |
| 2008/0077217 A1 | 3/2008 | Santamore et al. |
| 2008/0234771 A1 | 9/2008 | Chinchoy et al. |
| 2008/0269820 A1 | 10/2008 | Akersberga |
| 2008/0269825 A1 | 10/2008 | Chinchoy et al. |

*Primary Examiner* — Brian T Gedeon
(74) *Attorney, Agent, or Firm* — Schwegman Lundberg & Woessner, P.A.

(57) ABSTRACT

An apparatus comprises an implantable sensor and a signal analyzer circuit communicatively coupled to the implantable sensor. The implantable sensor is configured for coupling to an implantable lead and the implantable sensor provides an electrical vibration sensor signal representative of mechanical vibration of the implantable lead. The signal analyzer circuit is configured to determine a baseline of the vibration sensor signal, detect a change in the vibration sensor signal from the baseline vibration sensor signal, and provide an indication of the change to a user or process.

20 Claims, 6 Drawing Sheets

METHOD AND APPARATUS FOR SENSING MECHANICAL ENERGY OF AN IMPLANTABLE LEAD

CROSS-REFERENCE TO RELATED APPLICATION

This application claims the benefit of U.S. Provisional Application No. 61/243,683, filed on Sep. 18, 2009, under 35 U.S.C. §119(e), which is incorporated herein by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition.

The devices may include one or more electrodes in communication with one or more sense amplifiers to monitor electrical heart activity within a patient and may include one or more of the electrodes on an implantable lead. IMDs often include one or more sensors to monitor one or more other internal patient parameters. Monitoring heart activity and other internal patient parameters may provide early, if not immediate, diagnosis of cardiac disease.

OVERVIEW

This document relates generally to systems, methods, and devices for improved monitoring of cardiac function of a patient or subject, and in particular for monitoring of cardiac function using detected mechanical cardiac vibration.

In example 1, an apparatus includes an implantable sensor and a signal analyzer circuit communicatively coupled to the implantable sensor. The implantable sensor is configured for coupling to an implantable lead and the implantable sensor provides an electrical vibration sensor signal representative of mechanical vibration of the implantable lead. The signal analyzer circuit is configured to determine a baseline of the vibration sensor signal, detect a change in the vibration sensor signal from the baseline vibration sensor signal, and provide an indication of the change to a user or process.

In example 2, the apparatus of example 1 optionally includes a hermetically sealed housing, and a header attached to the hermetically sealed housing. The header is to receive the implantable lead, and the implantable sensor is located within the header adjacent to, and in mechanical communication with, a proximal end of the implantable lead.

In example 3, the apparatus of example 1 optionally includes a hermetically sealed housing, and a header attached to the hermetically sealed housing. The header is to receive the implantable lead, and the implantable sensor is configured to be attached to the implantable lead outside of the header and the hermetically sealed housing and at a proximal end of the implantable lead.

In example 4, the apparatus of example 1 optionally includes a hermetically sealed housing, and the implantable sensor is located within the hermetically sealed housing.

In example 5, the apparatus of any one of examples 1-4 is optionally for coupling to an implantable lead that is configured for placement through a heart valve. The implantable sensor is configured to provide an electrical sensor signal representative of mechanical vibration induced on the implantable lead by the heart valve impacting the implantable lead.

In example 6, the apparatus of example 5 optionally includes a therapy circuit, configured to provide electrical pacing therapy to the heart using the same or a different implantable lead, and a controller. The controller is communicatively coupled to the therapy circuit and the signal analyzer circuit, and is configured to initiate delivery of the electrical pacing therapy. The signal analyzer circuit is configured to verify, using the vibration sensor signal, that the electrical pacing therapy induces a depolarization of the heart.

In example 7, the apparatus of example 5 optionally includes a cardiac signal sensing circuit communicatively coupled to the signal analyzer circuit and a therapy circuit. The cardiac signal sensing circuit is configured to provide a sensed cardiac signal representative of cardiac depolarization events of a subject. The therapy circuit is configured to provide high-energy cardioversion or defibrillation shock therapy to the heart using the same or a different implantable lead. The controller is communicatively coupled to the therapy circuit and the signal analyzer circuit. The signal analyzer circuit is configured to detect a tachyarrhythmia using the cardiac signal, and determine, using the vibration signal, whether the detected tachyarrhythmia is hemodynamically stable or hemodynamically unstable. The controller is configured to initiate delivery of shock therapy when the detected tachyarrhythmia is determined to be unstable.

In example 8, the apparatus of claim 5 optionally includes a therapy circuit configured to provide electrical resynchronization pacing therapy to the heart using the same or a different implantable lead. The controller is communicatively coupled to the therapy circuit and the signal analyzer circuit, and the controller is configured to initiate delivery of the electrical resynchronization pacing therapy. The signal analyzer circuit is configured to determine, using the vibration sensor signal, an efficacy of the of the electrical resynchronization therapy.

In example 9, the implantable sensor of any one of examples 5-9 optionally is a first implantable sensor providing a first vibration sensor signal. The apparatus of any of the examples optionally includes a hermetically sealed housing and a second implantable sensor configured to provide a second electrical sensor signal representative of mechanical vibration at the hermetically sealed housing. The first vibration sensor signal includes a composite electrical signal representative of the mechanical vibration induced on the implantable lead by a heart valve impacting the implantable lead and of mechanical vibration at the hermetically sealed housing. The signal analyzer circuit is configured to extract a vibration signal substantially only induced on the implantable lead by the heart valve by a comparison of the first and second vibration sensor signals.

In example 10, the signal analyzer circuit of any one of examples 1-9 is optionally configured to determine a resonant frequency of the implantable lead, detect a change in the amplitude of the vibration sensor signal at the resonant frequency, and provide the indication when the change in the amplitude of the vibration sensor signal satisfies a specified amplitude change threshold.

In example 11, the apparatus of any one of examples 1-10 optionally includes an actuating device to induce the mechanical vibration on the implantable lead. The implantable sensor is configured to provide an electrical sensor signal representative of a reflection on the implantable lead of the mechanical vibration induced by the actuating device.

In example 12, the actuating device of example 11 is optionally configured to receive operating power from energy telemetered by a separate device.

In example 13, a method includes obtaining, using an IMD, an electrical vibration signal representative of mechanical vibration that is induced on an implantable lead, determining a baseline vibration signal, detecting a change in the vibration signal from the baseline vibration signal, and providing an indication of the change to a user or process.

In example 14, the obtaining a vibration sensor signal of claim 13 optionally includes obtaining an electrical vibration signal representative of mechanical vibration induced on the implantable lead by a heart valve impacting the implantable lead.

In example 15, the method of example 14 optionally includes delivering electrical pacing therapy with the IMD, and verifying, using the vibration signal, that the electrical pacing therapy induces a depolarization of the heart.

In example 16, the method of any one of examples 14-15 optionally includes sensing a cardiac signal using the IMD, wherein the cardiac signal is representative of cardiac depolarization events of a subject, detecting a tachyarrhythmia using the cardiac signal, and determining, using the vibration signal, whether the detected tachyarrhythmia is hemodynamically stable or hemodynamically unstable.

In example 17, the obtaining the vibration signal of any one of examples 14-16 optionally includes obtaining a first composite electrical vibration signal representative of the mechanical vibration induced on the implantable lead by a heart valve impacting the implantable lead and of mechanical vibration at a housing of the IMD. The method of any of the examples optionally includes obtaining, with the IMD, a second electrical signal representative of mechanical vibration that is induced at a housing of the IMD, and extracting a vibration signal representative of vibration substantially only induced on the implantable lead by the heart valve by a comparison of the first and second vibration signals.

In example 18, the determining a baseline vibration signal of any one of examples 13-17 optionally includes determining a resonant frequency of the implantable lead, the detecting a change in the vibration signal of any of the examples optionally includes detecting a change in amplitude of the vibration signal at the resonant frequency from an amplitude of the baseline vibration signal, and the providing an indication of the change to a user or process of the any of the examples optionally includes providing an alert to a user or process upon detecting a change in the amplitude of the vibration signal that satisfies a specified amplitude change threshold.

In example 19, the obtaining an electrical signal representative of mechanical vibration of any one of examples 13-18 optionally includes inducing a mechanical vibration on the implantable lead using the IMD, obtaining an electrical vibration signal representative of a reflection on the implantable lead of the induced mechanical vibration, and evaluating lead integrity using the reflected electrical vibration signal.

In example 20, the inducing a mechanical vibration of example 19 optionally includes inducing a resonant mechanical vibration on the implantable lead, the determining a baseline vibration signal optionally includes establishing a baseline vibration signal of the reflected electrical vibration signal at the resonant frequency, and the evaluating lead integrity optionally includes obtaining a reflected electrical vibration signal at the resonant frequency and determining whether there is a change in the electrical vibration signal from the baseline vibration signal at the resonant frequency.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for improved detection of cardiac events by an IMD. Specifically systems and methods for improved detection of arrhythmias by an IMD are described.

An IMD may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
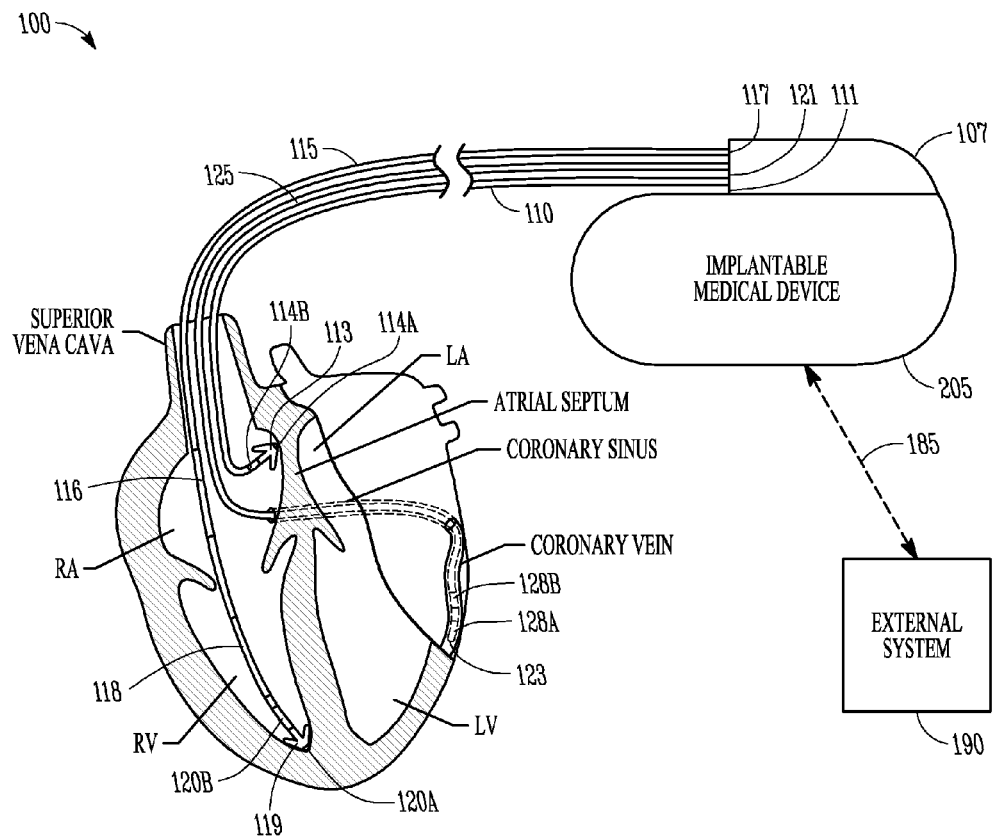
FIG. 1 is an illustration of an example of portions of a system that includes an IMD.

FIG. 1 is an illustration of portions of a system 100 that uses an IMD 105. Examples of the IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown can be used to detect and treat a cardiac arrhythmia such as tachyarrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed housing or "can." System 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. Proximal end 111 is coupled to a header connector 107 of the IMD 105. Distal end 113 is configured for placement in the RA in or near the atrial septum. RA lead 110 may include a pair of bipolar electrodes, such as an RA tip electrode 114A and an RA ring electrode 114B. RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage.

The example shown also includes right ventricular (RV) lead 115 having a proximal end 117 and a distal end 119. Proximal end 117 is coupled to header connector 107. Distal end 119 is configured for placement in the RV. The RV lead 115 shown passes through the tricuspid valve. RV lead 115 may include one or more of a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA or the superior vena cava. Defibrillation electrode 118 is incorporated into the lead body near distal end 119 for placement in the RV. RV electrodes 120A and 120B may form a bipolar electrode pair and are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or an electrode formed on the can of IMD 105 allow for delivery of cardioversion/defibrillation pulses to the heart.

RV tip electrode 120A, RV ring electrode 120B, and/or an electrode formed on the can of IMD 105 allow for sensing an RV electrogram indicative of RV depolarizations and delivering RV pacing pulses. RA tip electrode 114A, RA ring electrode 114B, and/or an electrode formed on the can of IMD 105 allow for sensing an RA electrogram indicative of RA depolarizations and delivering RA pacing pulses. Sensing and pacing allows the IMD 105 to adjust timing of the heart chamber contractions. In some device examples, IMD 105 can adjust the timing of ventricular contractions with respect to the timing of atrial contractions delay by sensing a contraction in the RA and pacing the RV at the desired atrial-ventricular (AV) delay time.

Also shown is a left ventricular (LV) lead 125. LV lead 125 is a coronary pacing and/or sensing lead that includes an elongate lead body having a proximal end 121 and a distal end 123. Proximal end 121 is coupled to header connector 107. Distal end 123 is configured for placement or insertion in the coronary vein. LV lead 125 may include an LV ring or tip electrode 128A and an LV ring electrode 128B. The distal portion of LV lead 125 is configured for placement in the coronary sinus and coronary vein such that LV electrodes 128A and 128B are placed in the coronary vein. LV electrodes 128A and 128B may form a bipolar electrode pair and are incorporated into the lead body at distal end 123 and each electrically coupled to IMD 105 through a conductor extending within the lead body. LV tip electrode 128A, LV ring electrode 128B, and/or an electrode formed on the can of IMD 105 allow for sensing an LV electrogram indicative of LV depolarizations and delivering LV pacing pulses. Note that although a specific arrangement of leads and electrodes are shown the illustration, the present methods and systems will work in a variety of configurations and with a variety of electrodes.

The implantable leads described are typically used to sense electrical cardiac activity or to deliver electrical energy to the heart. Monitoring cardiac activity provides important diagnostic information related to cardiac disease. Additional information can be provided by monitoring mechanical vibration sensed on the implantable leads. Vibrational energy from physical motion of the heart may be transferred to the implantable leads of FIG. 1. For example, impingement on the RV lead 115 by the tricuspid valve of the heart may be transferred to the lead. The induced vibration can be monitored because the propagation speed of the resulting vibration is proportional to the density of the conducting medium. Analogous to a train track vibrating long before a train can be heard via sound waves in air, the metal coil of some implantable leads carry the vibration more efficiently than the surrounding tissue and blood. The implanted lead acts as a mechanical amplifier of the vibration and preserves the high fidelity component of the signal whereas the tissue and blood attenuates the signal.

Forces directly applied to the lead excite mechanical resonant modes that can transfer along the lead. This is somewhat analogous to striking a train track with a hammer. The hammer strike excites longitudinal resonant modes in the train track and transmits sound over a wide frequency range; including the natural resonant frequency of the train track. The implanted lead is the "train track" and the tricuspid valve is the "hammer." Of course, this is just a simplified analogy to demonstrate the concept of a resonant mode in an implantable lead. The lead typically resonates at a frequency higher than other natural body sounds. Thus, the vibration can be detected by monitoring for vibration of the implantable lead at the resonant frequency or at a higher frequency.

Figure 2A:
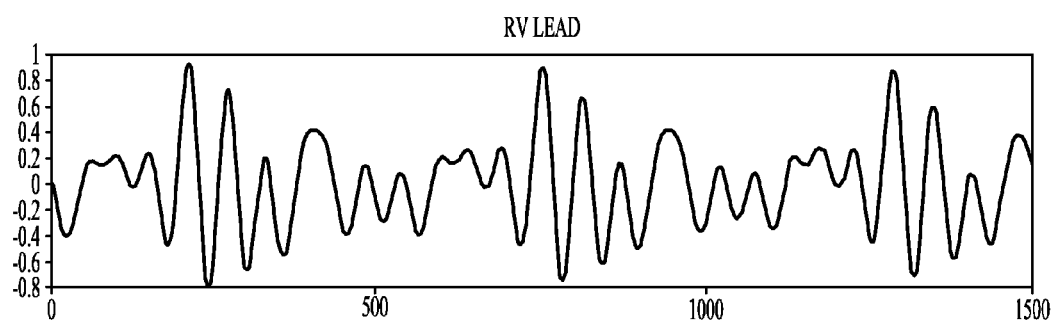
FIGS. 2A-2C show graphs of electrical signals representative of mechanical vibration.
Figure 2B:
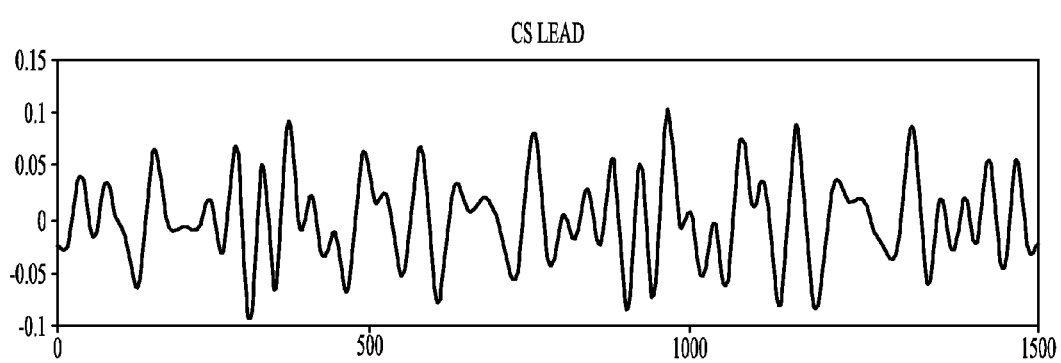
Figure 2C:
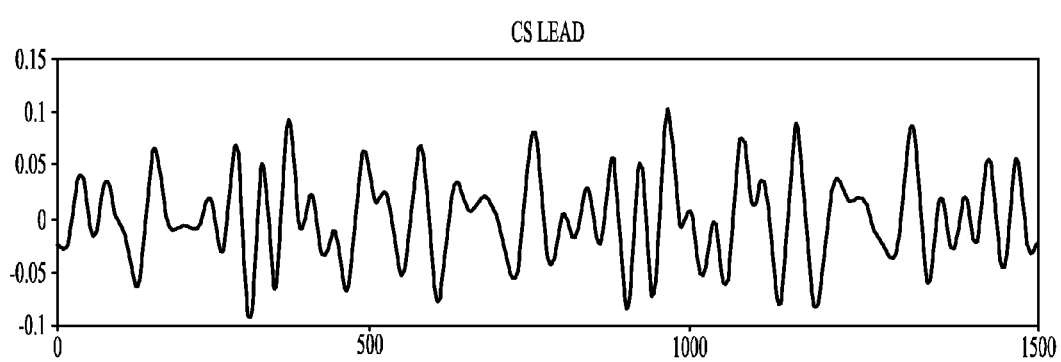

FIG. 2 shows graphs of electrical signals representative of mechanical vibration transferred to an implantable lead from physical motion of the heart. The signals were obtained by placing a vibration sensor in contact with an implanted lead. FIG. 2A shows a graph of a vibration signal obtained from a vibration sensor in contact with a lead implanted in the apex of the right ventricle. The graph was obtained by filtering the signal with a bandpass filter having a bandwidth of 5-20 Hz and averaging the signal over sixty heartbeats. FIG. 2B shows a graph of a vibration signal obtained from a vibration sensor in contact with a lead implanted in the coronary sinus of the heart. This graph was obtained by filtering the signal with a bandpass filter having a bandwidth of 5-30 Hz and averaging the signal over eighty heartbeats. FIG. 2C is a reference graph obtained from an accelerometer secured on the subject's chest.

This vibrational information may contain useful diagnostic information. For example, if the mechanical energy incident to the lead is from a heart valve impacting the lead, a high amplitude vibration may indicate a strong cardiac contraction. If the IMD provides pacing therapy, an increase in amplitude of the vibration energy can provide verification that pacing therapy provided by the IMD is inducing capture in the heart. In another example, if the IMD is designed to detect tachyarrhythmia, a decrease in vibration amplitude during tachyarrhythmia may be due to weak cardiac depolarization, which may indicate that the tachyarrhythmia is hemodynamically unstable. In still another example, if the IMD is designed to provide CRT, the strength of the vibration signal may provide an indication of the efficacy of the therapy.

Figure 3:
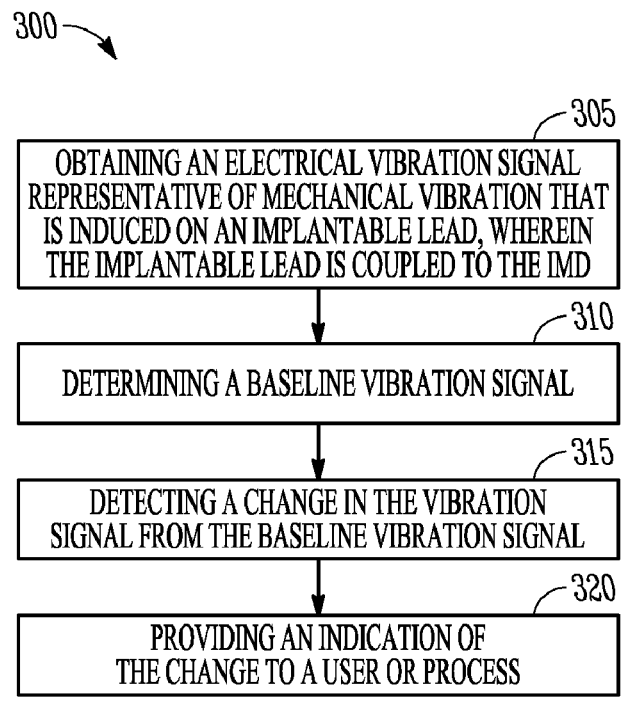
FIG. 3 shows a flow diagram of an example of a method of monitoring mechanical vibration using an implantable lead.

FIG. 3 shows a flow diagram of an example of a method 300 of monitoring mechanical vibration using an implantable lead. At block 305, an electrical vibration signal is obtained using an IMD. The vibration signal is representative of mechanical vibration that is induced on an implantable lead that is coupled to the IMD.

At block 310, a baseline vibration signal is determined. In some examples, the baseline vibration signal is established by forming an ensemble or other average of multiple sampled values of the vibration signal. In some examples, the baseline vibration signal is established by determining the central tendency of multiple sampled values of the vibration signal.

At block 315, a change in the vibration signal from the baseline vibration signal is detected. At block 320, an indication of the change is provided to a user or process. As discussed previously, a change from the baseline (e.g., a change in amplitude) may provide useful information related to efficacy of a therapy being delivered to the patient.

Figure 4:
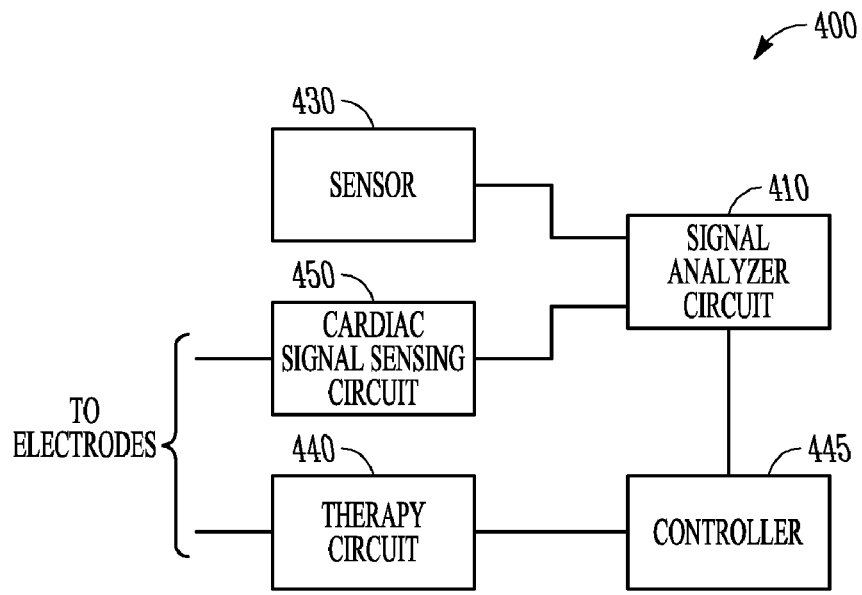
FIG. 4 is a block diagram of portions of an example of a device to monitor mechanical vibration induced on an implantable lead.

FIG. 4 is a block diagram of portions of an example of a device 400 to monitor mechanical vibration induced on an implantable lead. The device 400 includes an implantable sensor 430 and a signal analyzer circuit 410. The implantable sensor 430 is configured for coupling to an implantable lead, and the implantable sensor 430 provides an electrical vibration sensor signal representative of mechanical vibration of the implantable lead. A non-exhaustive list of examples of the implantable sensor 430 includes a microphone, a transducer, a pressure sensor, a strain sensor, a force sensor, and a displacement sensor.

Figure 5:
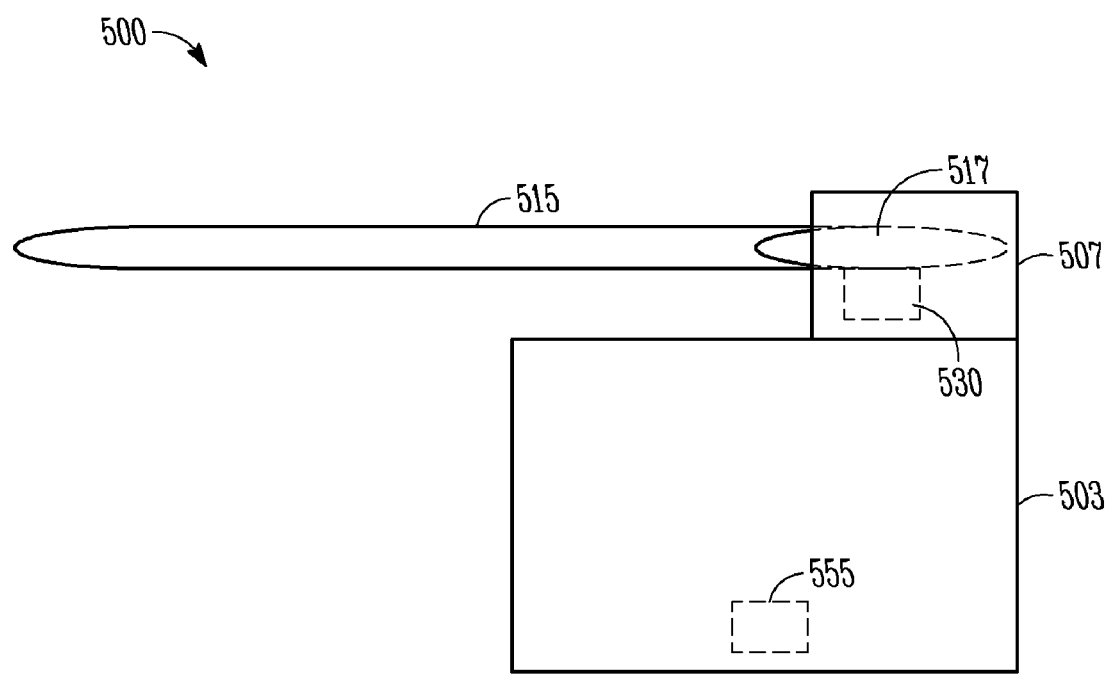
FIG. 5 is an illustration of an example of a device that includes an implantable sensor.

FIG. 5 is an illustration of an example of a device 500 that includes an implantable sensor 530. The device 500 includes a hermetically sealed housing 503 and a header 507 attached to the housing 503. The header 507 receives the proximal end 517 of the implantable lead 515. The proximal end 517 may include a lead pin that is typically secured to the header 507. In certain examples, the proximal end 517 is secured by a set screw, but the described arrangements may include screwless connectors as well. The implantable sensor 530 is located within the header 507 adjacent to, and in electrical communication with, the proximal end 517 of the implantable lead 515. The mechanical communication provides for a mechanical vibration induced in the implantable lead 515 to be sensed by the implantable sensor 530.

Figure 6:
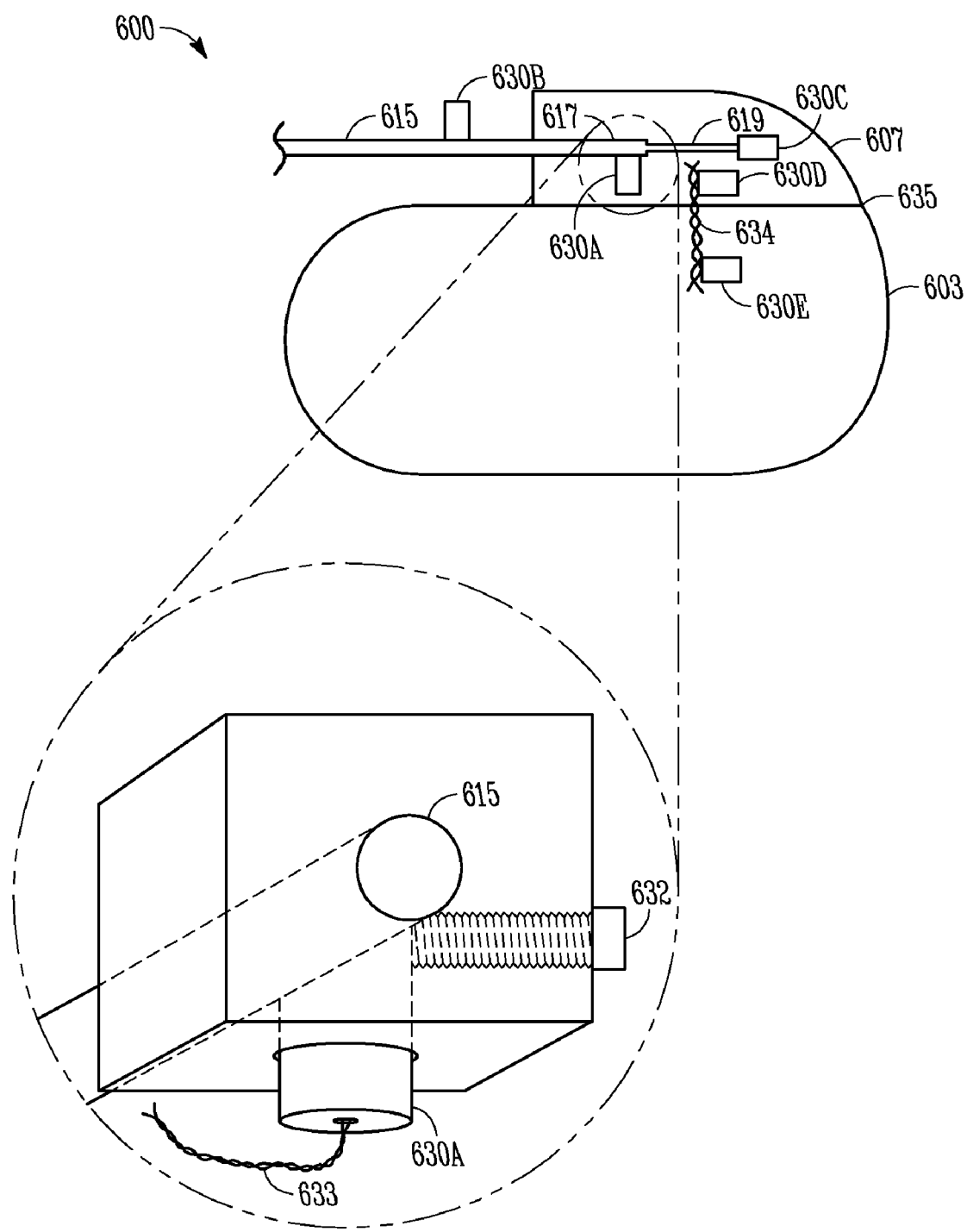
FIG. 6 is an illustration of another example of a device that includes an implantable sensor.

FIG. 6 is an illustration of another example of a device 600 that includes an implantable sensor. The device 600 includes a hermetically sealed housing 603 and a header 607 attached to the housing 603. The header 607 receives the proximal end 617 of the implantable lead 615. In the example shown, the proximal end 617 is secured by a set screw 632. The illustration shows optional placements for the implantable sensor. In some examples, an implantable sensor 630A is located within the header 607 adjacent to a side of proximal end 617 of the lead. The implantable sensor 630A shown in the blow-up view includes a two-wire connection 633.

In some examples, an implantable sensor 630B is attached to the implantable lead and located outside of the header 607 and hermetically sealed housing 603. The implantable sensor 630B is placed adjacent a proximal end of the implantable lead. Typically the implantable sensor 630B is separate from the implantable lead 615. This allows the device 600 to be used with leads that don't include an integral sensor.

In some examples, an implantable sensor 630C is located within the header 607 and parallel to the end of the implantable lead 615. In certain examples, the implantable lead 615 includes a lead pin 619 and the implantable sensor 630C is adjacent the lead pin 619.

In some examples, an implantable sensor 630D is located within the header 607 but not adjacent to the proximal end 617 of the lead. The mechanical vibration is sensed on the electrical conductors 634 running from the implantable lead 615 to the electronics contained within the hermetically sealed housing and on the hermetic side of the hermetic seal 635. In some examples, an implantable sensor 630E is located within the hermetically sealed housing and on the hermetic side of the hermetic seal 635.

Returning to FIG. 4, the signal analyzer circuit 410 is communicatively coupled to the implantable sensor 430. The communicative coupling allows the signal analyzer circuit 410 to communicate signals with the implantable sensor 430 even though there may be intervening circuitry. In certain examples, the signal analyzer circuit 410 includes a processor, such as a microprocessor, a digital signal processor, or other kind of processor. In certain examples, the signal analyzer circuit 410 includes an application specific integrated circuit (ASIC). In certain examples, the signal analyzer circuit 410 performs the described functions by performing instructions embodied in software, firmware, or hardware, or any combination of software, firmware, and hardware.

The signal analyzer circuit 410 determines a baseline of the vibration sensor signal provided by the implantable sensor 430. In some examples, the signal analyzer circuit 410 establishes the baseline by determining a central tendency of multiple sampled values of the vibration signal. In certain examples, the central tendency includes forming an ensemble or other average of the multiple sampled values.

When the signal analyzer circuit 410 detects a change in the vibration sensor signal from the baseline vibration sensor signal, the signal analyzer circuit 410 provides an indication of the change to a process or user. The process may be running on the signal analyzer circuit 410 or may be running on a different component of the device 400. In certain examples, the device 400 provides the indication to a user by communicating the indication to an external device.

In some examples, the signal analyzer circuit 410 determines a resonant frequency of the implantable lead and detects a change in the amplitude of the vibration sensor signal at the determined resonant frequency. The signal analyzer circuit 410 provides the indication to the process or user when the change in the amplitude of the vibration sensor signal satisfies a specified amplitude change threshold. The resonant frequency depends on design of the lead. The resonant frequency of the lead can typically be in the range of 200 Hz to 600 Hz, with leads designed to provide shock therapy at the lower end of the scale and leads designed to provide pacing therapy at the higher end of the scale. In certain examples, the signal analyzer circuit 410 includes signal filters that are optimized to detect the resonant frequency of a specific lead or lead type.

According to some examples, the implantable sensor 430 is in mechanical communication with an implantable lead configured for placement through a heart valve, such as RV lead 115 in FIG. 1. The implantable sensor 400 provides an electrical sensor signal representative of mechanical vibration induced on the implantable lead by the heart valve impacting the implantable lead.

The sensed electrical vibration sensor signal may include noise or other vibration signal components that may originate from sources other than the lead. For instance, the vibration sensor signal may be a composite electrical signal representative of the mechanical vibration induced on the implantable lead by a heart valve impacting the implantable lead and of mechanical vibration at one or more of a hermetically sealed housing of the device 400 and a header attached to the housing of the device 400.

In some examples, the device 400 includes a second implantable sensor. The second implantable sensor senses vibration from sources other than an implanted lead. FIG. 5 shows an example of a second implantable sensor 555. In the example, the second implantable sensor 555 is formed on the hermetically sealed housing 503 of the device 500. The second implantable sensor 555 provides a second electrical sensor signal representative of mechanical vibration at the hermetically sealed housing. This second electrical sensor signal is a combination of mechanical vibration induced on the implantable lead by a heart valve impacting the implantable lead and of mechanical vibration at the hermetically sealed housing 503 of the device 500.

Returning to FIG. 4, in some examples the signal analyzer circuit 410 extracts a vibration signal that is substantially only induced on the implantable lead by the heart valve by a comparison of the first vibration sensor signal produced by implantable sensor 430 and the second vibration sensor signal. In certain examples, the signal analyzer circuit 410 subtracts the second sensor signal from the composite signal to extract the vibration signal.

In certain examples, the second implantable sensor is located in a header of the device that is attached to the housing, and the second electrical sensor signal is a combination of mechanical vibration induced on the implantable lead by a heart valve impacting the implantable lead and of mechanical vibration at the header. Again the signal analyzer circuit 410 extracts the vibration signal that is substantially only induced on the implantable lead by the heart valve by a comparison of the first and second vibration sensor signals. In certain examples, the device includes both an implantable sensor formed on the housing and an implantable sensor located in the header, and the signal analyzer circuit 410 compares three sensor signals to extract the vibration signal that is substantially only induced on the implantable lead by the heart valve.

According to some examples, the device 400 is a CFM device and includes a therapy circuit 440 that provides electrical pacing therapy to the heart using the same or a different implantable lead than the lead in mechanical communication with the implantable sensor 430. The device also includes a controller 445 communicatively coupled to the therapy circuit 440 and the signal analyzer circuit 410. In certain examples, the controller 445 includes a processor. In certain examples, the controller 445 and the signal analyzer circuit 410 are integral to the same processor. In certain examples, the controller 445 and the signal analyzer circuit 410 are integral to the same ASIC.

The controller 445 initiates delivery of the electrical pacing therapy by the therapy circuit 440. The signal analyzer circuit 410 is configured to verify, using the vibration sensor signal, that the electrical pacing therapy induces a depolarization of the heart. For instance, a strong cardiac depolarization will cause a strong closing of the valve that induces a strong vibration signal. In some examples, if the amplitude of the vibration signal (e.g., at resonance) drops below a threshold amplitude value, the signal analyzer circuit 410 generates the indication which may be an alert to indicate loss of capture. Loss of capture refers to the situation where a delivered pacing pulse fails to result in a depolarization of the heart. Conversely, if the vibration signal is used to verify capture, the indication may be that the sensed vibration signal is above a capture detection threshold value. These threshold values may be programmable in the device and may be set at time of implant according to measurements taken at that time.

According to some examples, the therapy circuit 440 provides electrical resynchronization pacing therapy to the heart and the controller 445 initiates delivery of the electrical resynchronization pacing therapy. The therapy is delivered using the same or a different implantable lead than the lead in mechanical communication with the implantable sensor 430. Using the vibration signal provided by the implantable sensor 430, the signal analyzer circuit 410 determines an efficacy of the of the electrical resynchronization therapy. For instance, the resynchronization therapy may be delivered to a right ventricle using an RV lead, such as RV lead 115 in FIG. 1. An increase in the amplitude of the vibration signal as a result of the therapy may indicate a stronger closing of the heart valve which in turn can indicate that the therapy is producing stronger contractions. Conversely, no increase or a decrease in amplitude may indicate that the therapy is not improving heart depolarization.

In another example, the resynchronization therapy may be delivered to a right ventricle using an RV lead and delivered to a left ventricle using an LV lead such as LV lead 110. The device 400 may include a first implantable vibration sensor in mechanical communication with the RV lead and a second implantable vibration sensor in mechanical communication with the LV lead. A cardiac depolarization in the right ventricle may cause a vibration on the RV lead and a cardiac depolarization in the right ventricle may cause a vibration on the LV lead. A comparison of the RV vibration signal and the LV vibration signal produced by the first and second vibration sensors (e.g., by comparing the time when maximum amplitude occurs in the vibration signals) may indicate whether the therapy is providing the proper timing of ventricular depolarizations.

According to some examples, the therapy circuit 440 provides high-energy cardioversion or defibrillation shock therapy to the heart and the controller 445 initiates delivery of the therapy. The therapy is delivered using the same or a different implantable lead than the lead in mechanical communication with the implantable sensor 430. For instance, the implantable lead may be an RV lead such as RV lead 115 in FIG. 1 that includes a proximal defibrillation electrode 116 and a distal defibrillation electrode 118.

The device 400 includes a cardiac signal sensing circuit 450 communicatively coupled to the signal analyzer circuit 410. The cardiac signal sensing circuit 450 provides a sensed cardiac signal representative of cardiac depolarization events of a subject. In some examples, the cardiac signal sensing circuit 450 is in electrical communication with electrodes on an implantable lead such as tip and ring electrodes 120A and 120B on RV lead 115 in FIG. 1. The implantable lead may be the same or a different lead from the lead in mechanical communication with the implantable sensor 430.

The signal analyzer circuit 410 may detect a tachyarrhythmia using the cardiac signal. Tachyarrhythmia includes abnormally rapid heart rate, or tachycardia, including ventricular tachycardia (VT) and supraventricular tachycardia (SVT). Tachyarrhythmia also includes rapid and irregular heart rate, or fibrillation, including ventricular fibrillation (VF). In certain examples, the signal analyzer circuit 410 detects an episode of tachyarrhythmia by detecting a sudden increase in a heart depolarization rate that exceeds a specified heart rate detection threshold. In certain examples, once the heart rate detection threshold is exceeded, other detection methods may be used to confirm that a patient is indeed experiencing tachyarrhythmia. For instance, the signal analyzer circuit 410 may detect tachyarrhythmia using an assessment of heart rhythm stability when a subject experiences a sudden increase in depolarization rate. Examples of methods and systems to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference.

When the episode of tachyarrhythmia is detected, the signal analyzer circuit 410 may determine whether the detected tachyarrhythmia is hemodynamically stable or hemodynamically unstable using the vibration signal provided by the implantable sensor 430. In a normal cardiac cycle, incoming blood pushes on a heart valve. Turbulence from the filling is a factor in causing the heart vale to close during a contraction. During a hemodynamically stable arrhythmia, the cardiac valves impart mechanical forces on the lead, which cause vibrations to transfer down the lead to the sensor in the device. If the tachyarrhythmia is hemodynamically unstable, there is less filling and possibly fluttering of the ventricle which causes the valves to close with less intensity or to not close at all. Thus, vibrations on the lead are weaker, non-existent, or have different signal morphology. For instance, the vibration signal may have much lower amplitude if the heart valve is closing less forcefully than it closes when an arrhythmia is hemodynamically stable.

Hemodynamically unstable tachyarrhythmias should be shocked, while hemodynamically stable arrhythmias may not require any therapy or may require more conservative therapy (e.g., antitachycardia pacing, or ATP). Thus, the controller 445 initiates delivery of shock therapy when a detected tachyarrhythmia is determined to be hemodynamically unstable.

Mechanical vibrational energy induced on implanted leads can provide device diagnostic information as well. Failures in implanted leads are typically deduced after a number of inappropriate therapies are delivered by a medical device due to fractures in conductors of the leads. Failures in leads can also be detected by electrical testing of the leads. This testing typically looks for a change in lead impedance to determine fractures in conductors of the leads. However, an implantable lead may contain several electrical conductors. Electrical testing may not indicate a problem until after failure has occurred. Monitoring mechanical vibration of an implantable lead may provide early indication of a lead problem.

Failures in an implantable lead may also be caused by failures in the insulating material of the lead, such as abrasions or cracks in the material. The insulating material of the lead may have distinct resonant components, or may contribute to the primary resonant mode. Failures in the insulting material may alter the resonant frequency. Thus, the early onset of lead failures can be detected via changes in the resonant properties before any impedance changes in the conductors are detected.

Figure 7:
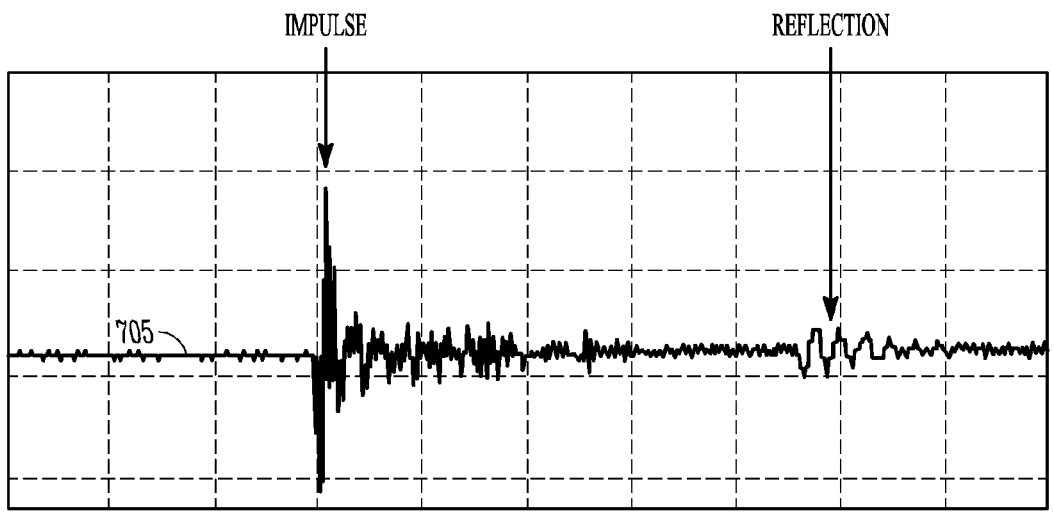
FIG. 7 shows an example of a graph of a vibration signal.

FIG. 7 shows an example of a graph of a vibration signal 705. The vibration signal 705 was sensed on a distal end of an implantable lead by a vibration sensor. The vibration signal shows an impulse vibration applied to the distal end of the lead with an actuating device. In this example, the actuating device was a solenoid. The impulse vibration travels down the lead and is reflected back to the distal end. The vibration signal 705 also shows a reflected vibration returning from the proximal end of the lead. Damage to the lead would be evident as a change or shift in the frequency response of the reflection, or may be evident as a change in amplitude of the reflected vibration.

It is desirable to know when the vibration is the result of the impulse and when the vibration signal is due to impact by a heart valve. Because the signal is obtained as a result of the applied impulse, it is possible to distinguish vibration induced by the applied impulse from vibration due to a heart valve. For instance, the impulse could be applied in a known time relationship to a heart depolarization in order separate the reflected signal from a valve closure event. Additionally, a change in the vibration signal due to lead damage may occur fairly quickly in comparison to a change in a vibration signal du to a problem heart valve closure. For example, damage to a lead as a result of being crushed by a clavicle of the patient will occur very quickly, whereas weakening of the vibration signal due to a problem with a heart valve will occur over months. Thus, the amount of time over which the change takes place may help distinguish failure in the lead from a heart valve problem.

Figure 8:
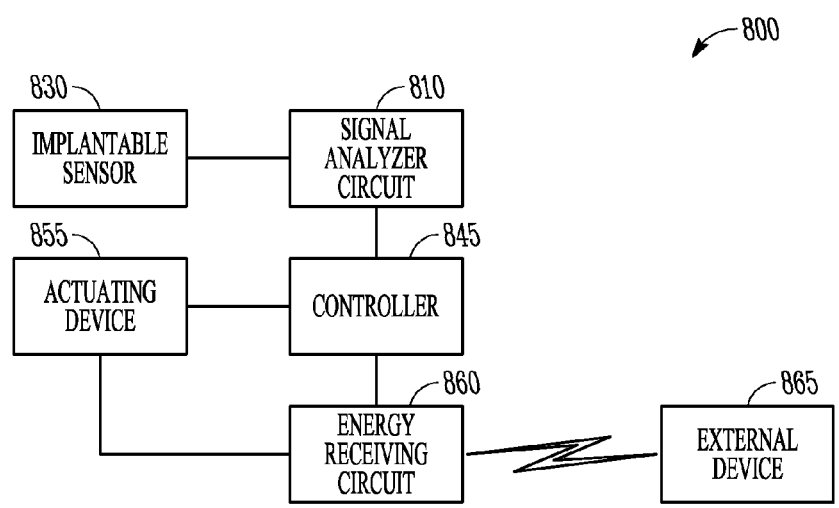
FIG. 8 is a block diagram of portions of another example of a device to monitor mechanical vibration induced on an implantable lead.

FIG. 8 is a block diagram of portions of another example of a device 800 to monitor mechanical vibration induced on an implantable lead. The device 800 includes an implantable sensor 830, a signal analyzer circuit 810, and a controller. The implantable sensor 830 is configured for coupling to an implantable lead. The device 800 also includes an actuating device 855 to induce the mechanical vibration on the implantable lead. An example of an actuating device is a transducer. A transducer generates mechanical movement in response to an applied electrical signal. In another example, the actuating device 855 includes a solenoid. In either example, application of an electrical drive signal to the actuating device causes the device to provide a mechanical impulse to the lead.

The distal end of the lead is coupled to the device 800. Impacting the distal end of the lead with the actuating device excites mechanical resonant modes of the lead that are reflected back to the device 800. The implantable sensor 830 provides an electrical vibration sensor signal representative of a reflection on the implantable lead of the mechanical vibration induced by the actuating device 855. The signal analyzer circuit 810 may include one or more signal filters that are optimized to detect electrical vibration signals at the resonant frequency of a specific lead or lead type. The controller 845 evaluates lead integrity using the reflected electrical vibration signal.

In some examples, the controller 845 evaluates lead integrity using a comparison to an established baseline vibration signal. The controller 845 establishes a baseline vibration signal of the reflected electrical vibration signal at the resonant frequency. The controller 845 determines lead integrity by obtaining (e.g., sampling) a reflected electrical vibration signal at the resonant frequency and determining whether there is a change in the electrical vibration signal from the baseline vibration signal at the resonant frequency. The change may include a change in the frequency response of the reflection, a change in amplitude of the reflected vibration, or both a change in frequency and a change in amplitude.

In some examples, operating power to drive the actuating device 855 is provided by the device, such as from a battery. In some examples, the energy to drive the actuating device 855 is provided by a separate device. FIG. 8 shows that the device 800 may include an energy receiving circuit 860 to receive operating power from energy telemetered by the external device 865. In some examples, the energy receiving circuit 860 and the external device 865 each include a coil antenna. Energy is transferred from the external device to the energy receiving circuit via mutual inductance linking the two coil antennas.

Because the resonant modes of vibration of an implantable lead may vary with lead type or may vary from lead to lead, the device may store a morphology of the reflected signal and determine failure of the lead from a change in the reflected signal from the stored signal morphology.

The controller 845 initiates monitoring of the mechanical vibration by initiating application of the impulse to the lead and measurement of the reflected vibration by the signal analyzer circuit 810. In some examples, the controller initiates a vibration measurement recurrently (e.g., daily). In some examples, the controller forms a trend of vibration measurements, or communicates the measurements to an external device which forms the trend. An alert may be generated when the trend of the vibration measurements are outside of a specified range, such as a frequency response being outside a frequency range or an amplitude of the signal being outside of an amplitude range.

It can be seen that valuable diagnostic information can be provided by monitoring mechanical vibration sensed on implanted subcutaneous leads. Monitoring the vibration may help in diagnosis of the patient's disease, in determining efficacy of treatment, and in monitoring the efficacy of the medical device itself.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
an implantable sensor configured for coupling to an implantable lead, wherein the implantable lead is configured for placement through a heart valve, and wherein the implantable sensor provides an electrical vibration sensor signal representative of mechanical vibration induced on the implantable lead by the heart valve impacting the implantable lead;
a signal analyzer circuit communicatively coupled to the implantable sensor, wherein the signal analyzer circuit is configured to:
determine a baseline of the vibration sensor signal induced by the heart valve;
detect a change in the vibration sensor signal from the baseline vibration sensor signal; and
provide an indication of the change to a user or process.

2. The apparatus of claim 1, including:
a hermetically sealed housing; and
a header attached to the hermetically sealed housing to receive the implantable lead, wherein the implantable sensor is located within the header adjacent to, and in mechanical communication with, a proximal end of the implantable lead.

3. The apparatus of claim 1, including:
a hermetically sealed housing; and
a header attached to the hermetically sealed housing to receive the implantable lead, wherein the implantable sensor is configured to be attached to the implantable lead outside of the header and hermetically sealed housing and at a proximal end of the implantable lead.

4. The apparatus of claim 1, including a hermetically sealed housing, and wherein the implantable sensor is located within the hermetically sealed housing.

5. The apparatus of claim 1, including:
a therapy circuit, configured to provide electrical pacing therapy to the heart using the same or a different implantable lead; and
a controller communicatively coupled to the therapy circuit and the signal analyzer circuit, wherein the controller is configured to initiate delivery of the electrical pacing therapy, and wherein the signal analyzer circuit is configured to verify, using the vibration sensor signal induced by the heart valve, that the electrical pacing therapy induces a depolarization of the heart.

6. The apparatus of claim 1, including:
a cardiac signal sensing circuit communicatively coupled to the signal analyzer circuit and configured to provide a sensed cardiac signal representative of cardiac depolarization events of a subject;

a therapy circuit, configured to provide high-energy cardioversion or defibrillation shock therapy to the heart using the same or a different implantable lead; and a controller communicatively coupled to the therapy circuit and the signal analyzer circuit, wherein the signal analyzer circuit is configured to:

detect a tachyarrhythmia using the cardiac signal; and determine, using the vibration signal, whether the detected tachyarrhythmia is hemodynamically stable or hemodynamically unstable, and wherein the controller is configured to initiate delivery of shock therapy when the detected tachyarrhythmia is determined to be unstable.

7. The apparatus of claim 1, including:

a therapy circuit, configured to provide electrical resynchronization pacing therapy to the heart using the same or a different implantable lead; and a controller communicatively coupled to the therapy circuit and the signal analyzer circuit, wherein the controller is configured to initiate delivery of the electrical resynchronization pacing therapy, and wherein the signal analyzer circuit is configured to determine, using the vibration sensor signal induced by the heart valve, an efficacy of the of the electrical resynchronization therapy.

8. The apparatus of claim 1, wherein the implantable sensor is a first implantable sensor providing a first vibration sensor signal, and where the apparatus includes:

a hermetically sealed housing; and a second implantable sensor configured to provide a second electrical sensor signal representative of mechanical vibration at the hermetically sealed housing, and wherein the first vibration sensor signal includes a composite electrical signal representative of the mechanical vibration induced on the implantable lead by a heart valve impacting the implantable lead and of mechanical vibration at the hermetically sealed housing, and wherein the signal analyzer circuit is configured to extract a vibration signal substantially only induced on the implantable lead by the heart valve by a comparison of the first and second vibration sensor signals.

9. The apparatus of claim 1, wherein the signal analyzer circuit is configured to:

determine a resonant frequency of the implantable lead;

detect a change in the amplitude of the vibration sensor signal at the resonant frequency; and provide the indication when the change in the amplitude of the vibration sensor signal satisfies a specified amplitude change threshold.

10. An apparatus comprising:

an implantable sensor configured for coupling to an implantable lead, wherein the implantable sensor provides an electrical vibration sensor signal representative of mechanical vibration of the implantable lead;

an actuating device to induce the mechanical vibration on the implantable lead, wherein the electrical vibration sensor signal is representative of a reflection on the implantable lead of the mechanical vibration induced by the actuating device; and a signal analyzer circuit communicatively coupled to the implantable sensor, wherein the signal analyzer circuit is configured to:

determine a baseline of the vibration sensor signal;

detect a change in the vibration sensor signal from the baseline vibration sensor signal; and provide an indication of the change to a user or process.

11. The apparatus of claim 10, wherein the signal analyzer circuit is configured to:

determine a resonant frequency of the implantable lead;

detect a change in the amplitude of the vibration sensor signal at the resonant frequency; and provide the indication when the change in the amplitude of the vibration sensor signal satisfies a specified amplitude change threshold.

12. The apparatus of claim 10, wherein the actuating device is configured to receive operating power from energy telemetered by a separate device.

13. A method comprising:

obtaining, using an implantable sensor of an implantable medical device (IMD), an electrical vibration signal representative of mechanical vibration induced on an implantable lead by a heart valve impacting the implantable lead, wherein the implantable lead is coupled to the IMD;

determining, using a signal analyzer circuit, a baseline vibration signal;

detecting a change in the electrical vibration signal from the baseline vibration signal; and providing an indication of the change to a user or process.

14. The method of claim 13, including:

delivering electrical pacing therapy with the IMD; and verifying, using the vibration signal, that the electrical pacing therapy induces a depolarization of the heart.

15. The method of claim 13, including:

sensing a cardiac signal using the IMD, wherein the cardiac signal is representative of cardiac depolarization events of a subject;

detecting a tachyarrhythmia using the cardiac signal; and determining, using the vibration signal, whether the detected tachyarrhythmia is hemodynamically stable or hemodynamically unstable.

16. The method of claim 13, wherein obtaining the vibration signal includes obtaining a first composite electrical vibration signal representative of the mechanical vibration induced on the implantable lead by a heart valve impacting the implantable lead and of mechanical vibration at a housing of the IMD, and wherein the method includes:

obtaining, with the IMD, a second electrical signal representative of mechanical vibration that is induced at a housing of the IMD; and extracting a vibration signal representative of vibration substantially only induced on the implantable lead by the heart valve by a comparison of the first and second vibration signals.

17. The method of claim 13, wherein determining a baseline vibration signal includes determining a resonant frequency of the implantable lead, wherein detecting a change in the vibration signal includes detecting a change in amplitude of the vibration signal at the resonant frequency from an amplitude of the baseline vibration signal, and wherein providing an indication of the change to a user or process includes providing an alert to a user or process upon detecting a change in the amplitude of the vibration signal that satisfies a specified amplitude change threshold.

18. A method comprising:

inducing a mechanical vibration on the implantable lead using an actuating device of an implantable medical device (IMD);

obtaining, using an implantable sensor of an implantable medical device (IMD), an electrical vibration signal representative of a reflection of the induced mechanical vibration on the implantable lead, wherein the implantable lead is coupled to the IMD;
evaluating, using a signal analyzer circuit communicatively coupled to the implantable sensor, lead integrity using the reflected electrical vibration signal; and
providing an indication of the lead integrity to a user or process.

19. The method of claim 18, including:
determining a baseline reflected vibration signal; and
detecting a change in the reflected vibration signal from the baseline reflected vibration signal,
wherein evaluating lead integrity includes evaluating lead integrity using the detected change in the reflected vibration signal.

20. The method of claim 19,
wherein inducing a mechanical vibration includes inducing a resonant mechanical vibration on the implantable lead,
wherein determining a baseline vibration signal includes establishing a baseline vibration signal of the reflected electrical vibration signal at the resonant frequency, and
wherein evaluating lead integrity includes obtaining a reflected electrical vibration signal at the resonant frequency and determining whether there is a change in the electrical vibration signal from the baseline vibration signal at the resonant frequency.

\* \* \* \* \*